(12) United States Patent
Yuan et al.

(10) Patent No.: US 11,988,311 B2
(45) Date of Patent: May 21, 2024

(54) STEEL WIRE AND TRANSMISSION SHAFT CONNECTING STRUCTURE, METHOD FOR CONNECTING THEREOF AND SURGICAL ROBOT

(71) Applicant: APEIRON SURGICAL CO., LTD., Shandong (CN)

(72) Inventors: Ping Yuan, Shandong (CN); Gaofeng Xu, Shandong (CN)

(73) Assignee: APEIRON SURGICAL CO., LTD., Shandong (CN)

( * ) Notice: Subject to any disclaimer, the term of this patent is extended or adjusted under 35 U.S.C. 154(b) by 218 days.

(21) Appl. No.: 17/621,699

(22) PCT Filed: Nov. 30, 2021

(86) PCT No.: PCT/CN2021/134563
§ 371 (c)(1),
(2) Date: Dec. 22, 2021

(87) PCT Pub. No.: WO2022/188476
PCT Pub. Date: Sep. 15, 2022

(65) Prior Publication Data
US 2023/0126698 A1   Apr. 27, 2023

(30) Foreign Application Priority Data
Mar. 10, 2021  (CN) .......................... 202110261447.4

(51) Int. Cl.
*A61B 17/00* (2006.01)
*F16L 3/10* (2006.01)
*F16M 11/04* (2006.01)

(52) U.S. Cl.
CPC .......... *F16L 3/1075* (2013.01); *F16M 11/041* (2013.01); *A61B 2017/00477* (2013.01); *F16C 2226/76* (2013.01); *F16C 2316/10* (2013.01)

(58) Field of Classification Search
CPC . A61B 2017/00477; A61B 2017/00486; F16C 2226/76; F16C 2316/10; F16M 11/041
See application file for complete search history.

(56) References Cited

U.S. PATENT DOCUMENTS

| | | | |
|---|---|---|---|
| 5,499,985 A | * | 3/1996 | Hein ..................... A61B 17/162 606/1 |
| 10,143,524 B2 | * | 12/2018 | Koch ............... A61B 17/00234 |

(Continued)

FOREIGN PATENT DOCUMENTS

| | | |
|---|---|---|
| CN | 101627921 | 1/2010 |
| CN | 102119872 | 7/2011 |

(Continued)

OTHER PUBLICATIONS

"Office Action of China Counterpart Application" with English translation thereof, dated Oct. 29, 2021, p. 1-p. 10.

(Continued)

*Primary Examiner* — Bradley Duckworth
(74) *Attorney, Agent, or Firm* — JCIP GLOBAL INC.

(57) ABSTRACT

The present invention relates to a steel wire and transmission shaft connecting structure, a surgical robot, and a method. A base is included. Multiple transmission shafts penetrate through the base. A clamping block is arranged at one end of the transmission shaft. The transmission shaft is detachably clamped and fixed to a quick-connect shaft through the clamping block and a clamping slot structure arranged at one end of the quick-connect shaft. The other end of the quick-connect shaft penetrates through a butting seat and is then detachably fixed to a steel wire extending from a pipeline member. A shifting clamp is arranged between the butting seat and the pipeline member. The shifting clamp is provided with a through hole configured for the butting shaft to (Continued)

penetrate through. The through hole is composed of a first hole portion and a second hole portion.

8 Claims, 9 Drawing Sheets

(56) References Cited

U.S. PATENT DOCUMENTS

| | | | | |
|---|---|---|---|---|
| 10,639,111 | B2 * | 5/2020 | Kopp | A61B 34/30 |
| 11,723,729 | B2 * | 8/2023 | Shelton, IV | A61B 90/37 |
| | | | | 700/247 |
| 2018/0243035 | A1 | 8/2018 | Kopp | |
| 2022/0249182 | A1 * | 8/2022 | Definis | A61B 17/128 |
| 2023/0263376 | A1 * | 8/2023 | Lo | A61B 1/0052 |
| | | | | 600/109 |

FOREIGN PATENT DOCUMENTS

| | | |
|---|---|---|
| CN | 203879882 | 10/2014 |
| CN | 105997254 | 10/2016 |
| CN | 208967432 | 6/2019 |
| CN | 209404833 | 9/2019 |
| CN | 110384556 | 10/2019 |
| CN | 110840564 | 2/2020 |
| CN | 111012385 | 4/2020 |
| CN | 111012407 | 4/2020 |
| CN | 211433290 | 9/2020 |
| CN | 113048137 | 6/2021 |
| DE | 102016117751 | 3/2018 |
| WO | 2020185524 | 9/2020 |

OTHER PUBLICATIONS

"Office Action of China Counterpart Application", dated Nov. 22, 2021, p. 1-p. 3.

"International Search Report (Form PCT/ISA/210) of PCT/CN2021/134563," dated Mar. 3, 2022, with English translation thereof, pp. 1-8.

"Written Opinion of the International Searching Authority (Form PCT/ISA/237) of PCT/CN2021/134563," dated Mar. 3, 2022, with English translation thereof, pp. 1-10.

* cited by examiner

STEEL WIRE AND TRANSMISSION SHAFT CONNECTING STRUCTURE, METHOD FOR CONNECTING THEREOF AND SURGICAL ROBOT

CROSS-REFERENCE TO RELATED APPLICATION

This application is a 371 of international application of PCT application serial no. PCT/CN2021/134563, filed on Nov. 30, 2021, which claims the priority benefit of China application no. 202110261447.4, filed on Mar. 10, 2021. The entirety of each of the above mentioned patent applications is hereby incorporated by reference herein and made a part of this specification.

TECHNICAL FIELD

The present invention relates to the technical field of medical equipment, and particularly to a steel wire and transmission shaft connecting structure, a surgical robot, and a method.

RELATED ART

Descriptions herein only provide background techniques related to the present invention, and do not necessarily constitute the related conventional art.

At present, steel wires and transmission shafts in a transmission mechanism of a surgical robot need to be sequentially assembled in one-to-one correspondence when being assembled. The inventor found that transmission mechanisms of existing surgical robots have the following defects.

A transmission mechanism cannot be butted and disassembled quickly after being mounted.

A quick-connect and quick-release separation end of the transmission structure mostly uses such a mode that a single driving member corresponds to a single driven member, and a mechanism using a mode that multiple driving members correspond to multiple driven members mostly need separate abutting, so long time is needed, and the efficiency is low.

A transmission connecting mechanism mostly transmits either a torque or a push-pull force separately, and when needing to simultaneously transmit the torque and the push-pull force, mostly uses multi-shaft transmission, so the structure is complex.

SUMMARY OF INVENTION

An objective of the present invention is to provide a steel wire and transmission shaft connecting structure capable of implementing the quick butting and disassembling of multiple transmission shafts and steel wires, to overcome the shortcomings of the prior art.

In order to realize the above objectives, the present invention adopts the technical scheme as follows:

According to a first aspect, the present invention provides a steel wire and transmission shaft connecting structure, which includes a base. Multiple transmission shafts penetrate through the base. A clamping block is arranged at one end of the transmission shaft. The transmission shaft is detachably clamped and fixed to a quick-connect shaft through the clamping block and a clamping slot structure arranged at one end of the quick-connect shaft. The other end of the quick-connect shaft penetrates through a butting seat and is then detachably fixed to a steel wire extending from a pipeline member. A shifting clamp is arranged between the butting seat and the pipeline member. The shifting clamp is provided with a through hole configured for the butting shaft to penetrate through. The through hole is composed of a first hole portion and a second hole portion. The quick-connect shaft moves between the first hole portion and the second hole portion, which can switch locked and unlocked states of the quick-connect shaft and the shifting clamp.

Further, the clamping block is of a T-shaped structure, including a first clamping block portion and a second clamping block portion which are perpendicular to each other. The first clamping block portion is fixedly connected to the transmission shaft.

Further, a T-shaped groove is provided in one end of the quick-connect shaft. A connecting portion fixed to the quick-connect shaft is arranged at a side portion of one side of an opening of the groove. The groove and the connecting portion form the clamping slot structure together such that the clamping block can be inserted into the groove from an opposite side of the connecting portion. The second clamping block portion extends from a space between the connecting portion and a bottom groove surface of the groove to implement the clamping fixation of the clamping block and the quick-connect shaft.

Further, the base is provided with a bump. The butting seat is provided with a fixed plate. A fixing hole is provided in the fixed plate. A buckle is further arranged on the butting seat. The bump can be inserted into the fixing hole at the same time when the clamping block is inserted into the groove. The buckle can be clamped and fixed to the base.

Further, a limiting slot is provided in a shaft surface of the quick-connect shaft to form a limiting portion that can be inserted into the through hole. The first hole portion is configured such that a hole surface thereof can fit an outer lateral surface of the limiting portion. A slot surface of the limiting slot can contact with the shifting clamp such that the first hole portion can limit the movement of the quick-connect shaft. The second hole portion is quick-connect configured to have a size larger than a section size of the quick-connect shaft such that the movement of the quick-connect shaft is not limited by the second hole portion.

Further, the butting seat is fixedly connected to the pipeline member.

Further, one end of the quick-connect shaft is detachably connected to the transmission shaft, while a connecting pin is inserted into the other end. The connecting pin is locked and fixed to the quick-connect shaft through a locking pin. The connecting pin is fixedly connected to the steel wire.

Further, the steel wire and the connecting pin are fixed by crimping.

According to a second aspect, the present invention provides a surgical robot, which is provided with the steel wire and transmission shaft connecting structure as described in the first aspect.

According to a third aspect, the present invention provides a method for connecting a steel wire and transmission shaft connecting structure, which includes:

pushing a shifting clamp such that a quick-connect shaft penetrates through a first hole portion, to limit the movement of the quick-connect shaft by the shifting clamp;

enabling the quick-connect shaft to move such that a clamping block at an end portion of a transmission shaft is embedded into a clamping slot structure, to complete the clamping fixation of the transmission shaft and the quick-connect shaft; and pushing the shifting clamp such that the quick-connect shaft penetrates through a second hole portion, to remove the limit of the shifting clamp to the movement of the quick-connect shaft.

The present invention has the following beneficial effects.

1: According to the connecting structure of the present invention, the movement of the quick-connect shaft can be limited by the first hole portion of the shifting clamp to locate the quick-connect shaft accurately. Therefore, the multiple transmission shafts and the multiple quick-connect shafts can be clamped and fixed simultaneously, the simultaneous connection of the multiple transmission shafts and the steel wires is implemented, and separate connection of the steel wires and the transmission shafts is avoided. The whole process is convenient and efficient, the practicability is higher, the operation is more labor-saving, and requirements on the quick connection and disassembling of driven members of multiple groups of transmission mechanisms in some situations are met.

2: According to the connecting structure of the present invention, with the clamping block and the clamping slot structure, the quick connection and disassembling of the multiple transmission shafts and the steel wires can be implemented while transmitting the torques and push-pull forces. Therefore, use requirements of the surgical robot are met.

3: According to the connecting structure of the present invention, one transmission shaft can transmit both a torque and a push-pull force. Therefore, the structure is simple.

BRIEF DESCRIPTION OF DRAWINGS

The accompanying drawings constituting a part of the present invention are used for providing further understanding for the present invention. Exemplary embodiments of the present invention and descriptions thereof are used for explaining the present invention and do not constitute a limitation to the present invention.

1—base; 2—bolt; 3—transmission shaft; 4—clamping block; 4-1—first clamping block portion; 4-2—second clamping block portion; 5—groove; 6—arc plate; 7—bump; 8—fixed plate; 9—fixing hole; 10—butting seat; 11—shifting clamp; 12—pipeline member; 13—steel wire; 14—connecting pin; 15—locking pin; 16—limiting portion; 17—first hole portion; 18—second hole portion; 19—quick-connect shaft; and 20—buckle.

DESCRIPTION OF EMBODIMENTS

It should be pointed out that the following detailed descriptions are all exemplary and intended to provide further descriptions about the present invention. Unless otherwise specified, all technical and scientific terms used herein have the same meaning as commonly understood by a person of ordinary skill in the art to which the present invention belongs.

It should be noted that terms used herein are only for describing specific implementations and are not intended to limit exemplary implementations according to the present invention. As used herein, the singular form is intended to include the plural form, unless the context clearly indicates otherwise. In addition, it should further be understood that terms "comprise" and/or "include" used in this specification indicate that there are features, steps, operations, devices, components, and/or combinations thereof.

For convenience of description, the words "above", "below", "left", and "right" only indicate directions consistent with those of the accompanying drawings, are not intended to limit the structure, and are used only for ease and brevity of illustration and description, rather than indicating or implying that the mentioned device or element must have a particular orientation or must be constructed and operated in a particular orientation. Therefore, such terms should not be construed as a limitation on the present invention.

As introduced in BACKGROUND, a common quick-connect and quick-release transmission structure mostly uses such a mode that a single driving member corresponds to a single driven member, and a mechanism using a mode that multiple driving members correspond to multiple driven members mostly need separate abutting, so long time is needed, and the efficiency is low. For the foregoing problem, the present invention discloses a steel wire and transmission shaft connecting structure.

Figure 1:
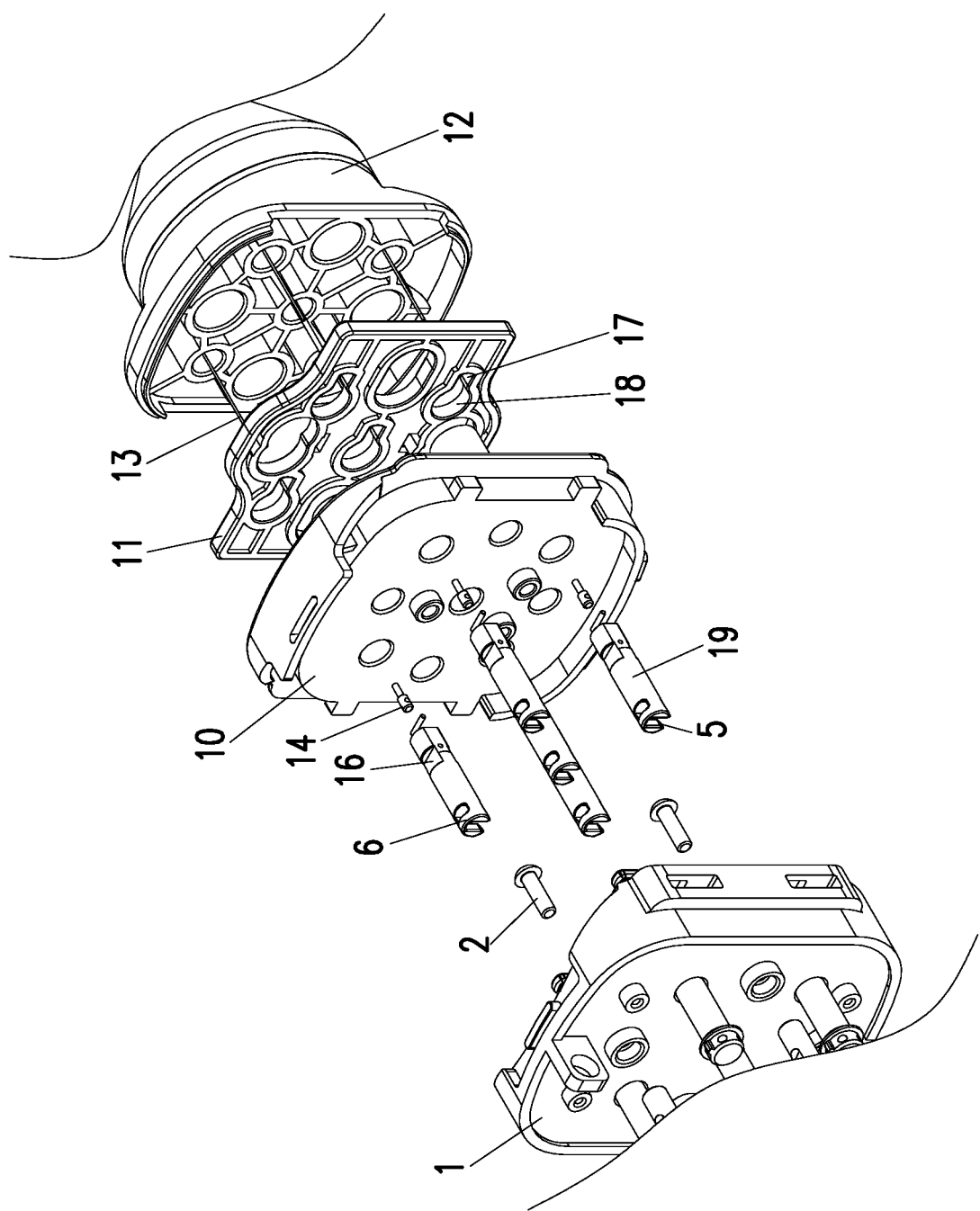
FIG. 1 is a first schematic exploded view of an overall structure according to Embodiment 1 of the present invention.
Figure 2:
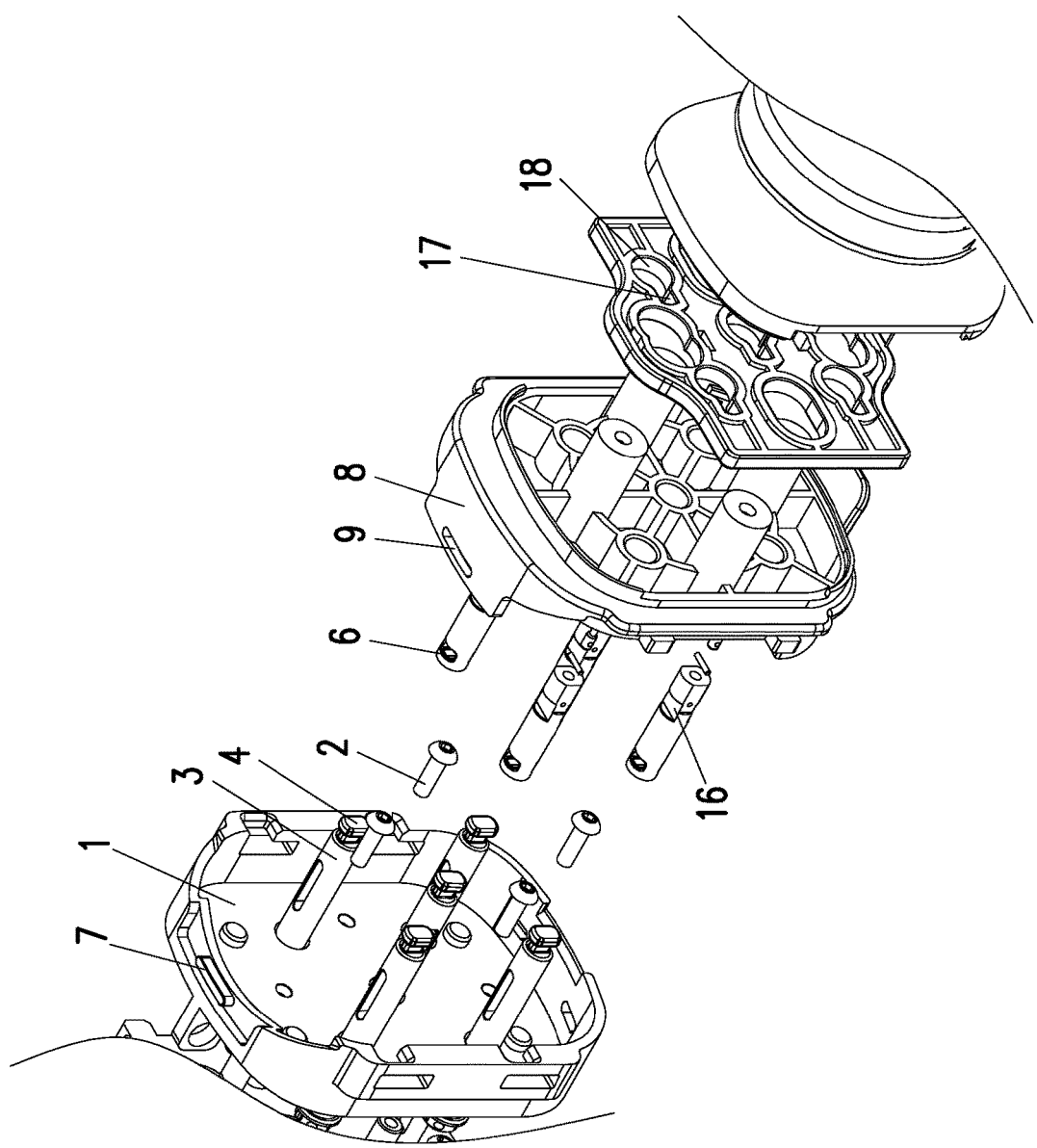
FIG. 2 is a second schematic exploded view of the overall structure according to Embodiment 1 of the present invention.
Figure 3:
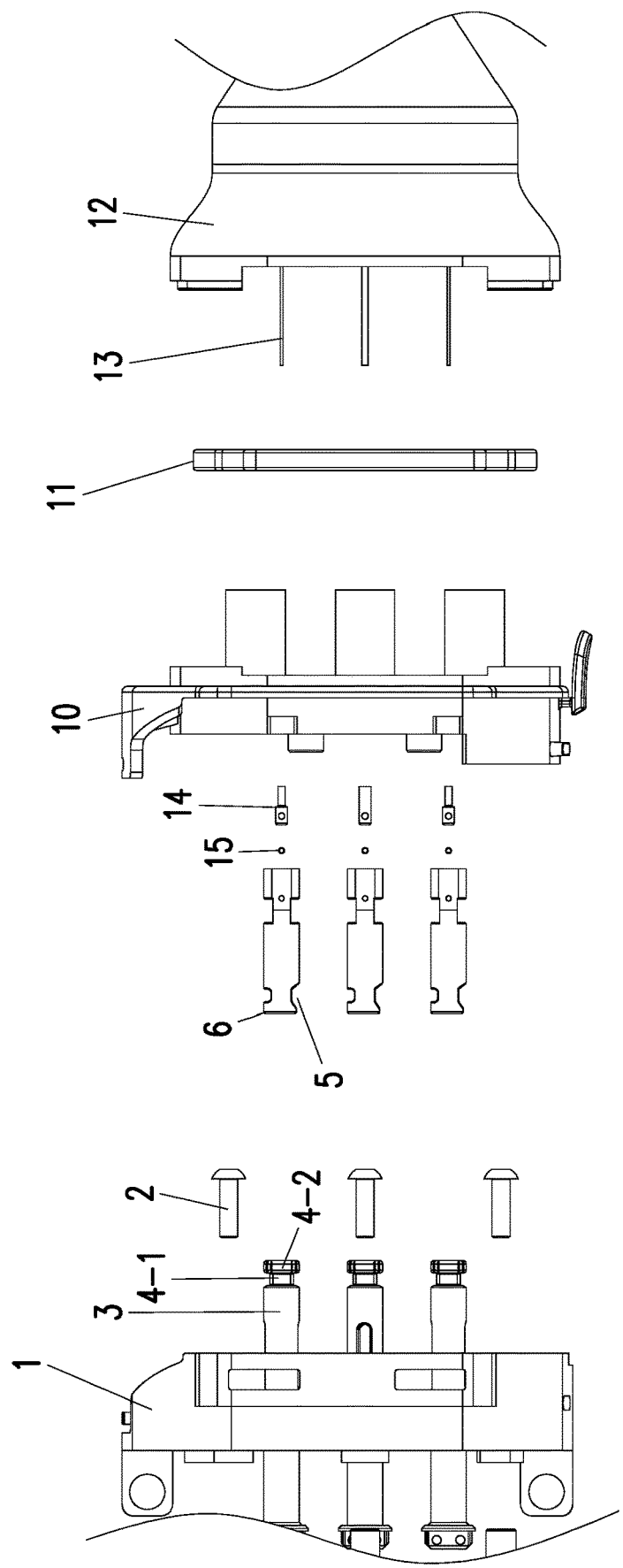
FIG. 3 is a third schematic exploded view of the overall structure according to Embodiment 1 of the present invention.
Figure 4:
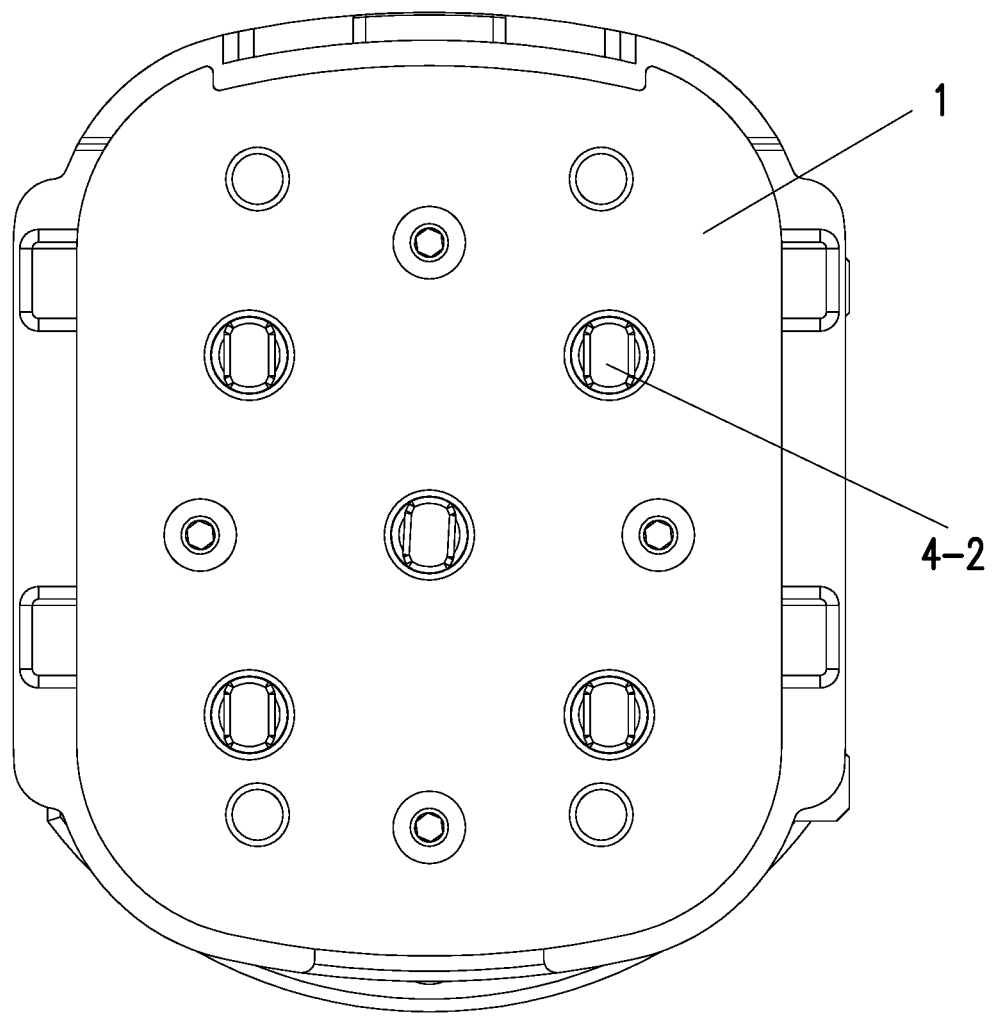
FIG. 4 is a side view of assembly of a base and transmission shafts according to Embodiment 1 of the present invention.
Figure 5:
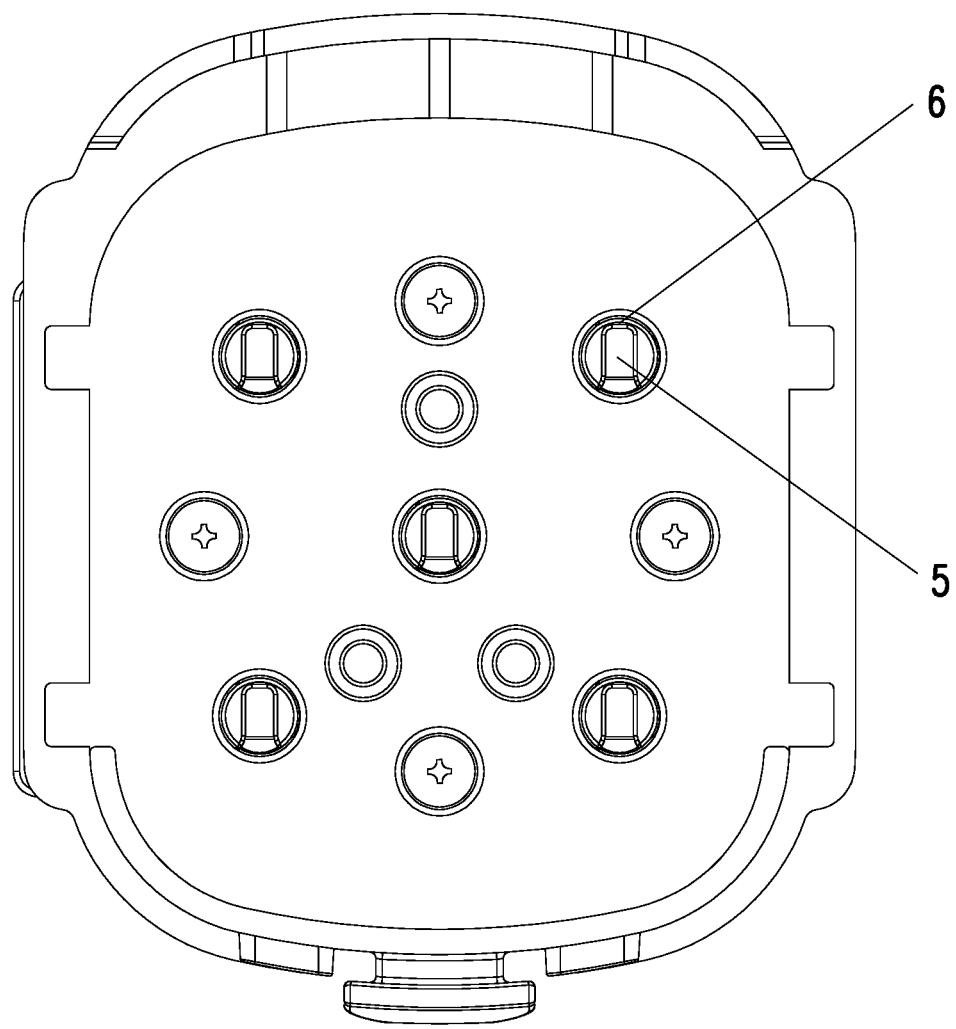
FIG. 5 is a side view of assembly of quick-connect shafts and a butting seat according to Embodiment 1 of the present invention.

Embodiment 1 is a typical implementation of the present invention. As shown in FIGS. 1 to 5, a steel wire and transmission shaft connecting structure includes a base, a transmission shaft, a quick-connect shaft, a steel wire, a butting seat, a pipeline member, and a shifting clamp.

The base 1 can be fixedly connected to the other structures by bolts 2. Multiple transmission shafts 3 penetrate through the base. The transmission shaft can be connected to a driving mechanism. The driving mechanism can drive the transmission shaft to rotate and move in its own axial direction.

In the present embodiment, there are five transmission shafts. Therefore, five matched quick-connect shafts and steel wires are arranged. The number of the transmission shafts can be set according to a practical usage requirement.

The quick-connect shaft 19 is arranged coaxially with the transmission shaft. A clamping slot structure is arranged at one end of the quick-connect shaft. A clamping block 4 matched with the clamping slot structure is arranged at an end portion of the transmission shaft. The clamping block can be clamped into the clamping slot structure to implement the detachable clamping fixation of the quick-connect shaft and the transmission shaft.

Preferably, the clamping block is of a T-shaped structure, including a first clamping block portion 4-1 and a second clamping block portion 4-2 which are perpendicular to each other. The first clamping block portion is fixedly connected to the end portion of the transmission shaft.

The clamping slot structure is matched with the clamping block. Specifically, a T-shaped groove 5 matched with a shape of the clamping block is provided in an end portion of the quick-connect shaft. A connecting portion is arranged at an upper-side position of an opening of the T-shaped groove. Preferably, the connecting portion uses an arch plate 6. Two ends of the arc plate are integrally connected to the quick-connect shaft. An outer lateral surface of the arc plate is flush with a shaft surface of the quick-connect shaft. An inner lateral surface of the arc plate is at a set distance from a groove surface of the groove.

With such arrangement, the quick-connect shaft can move from top to bottom such that the clamping block is inserted into the groove and the second clamping block portion is clamped into a space between the inner lateral surface of the arc plate and the groove surface of the groove. Therefore, the clamping fixation of the transmission shaft and the quick-connect shaft is implemented. Moreover, the rotation of the transmission shaft can drive the rotation of the quick-connect shaft, and the movement of the transmission shaft in its own axial direction can drive the movement of the quick-connect shaft in its own axial direction. Therefore, the transmission of torques and push-pull forces is implemented, and use requirements of a surgical robot are met.

In the present embodiment, a bump 7 is arranged at a top of the base. A fixed plate 8 is arranged at a top of the butting seat. A fixing hole 9 matched with the bump is provided in the fixed plate.

When the quick-connect shaft is driven by the butting seat to move from top to bottom to clamp the clamping block into the clamping slot structure, the bump can be inserted into the fixing hole. Therefore, the butting seat and the base are clamped to limit the movements of the butting seat and the base in the axial direction of the transmission shaft.

In addition, a buckle 20 is arranged at a bottom of the butting seat. An end portion of the buckle is a bevel. A bevel matched with the buckle is arranged at a bottom of the base. The butting seat drives the quick-connect shaft to move from top to bottom. The buckle can be deformed under the action of the bevel such that a top surface of the buckle finally contacts with a bottom surface of the base. Therefore, the clamping fixation of the buckle and the base is implemented to limit the movements of the butting seat and the base in a direction perpendicular to an axis of the transmission shaft.

One end of the quick-connect shaft is detachably fixedly connected to the transmission shaft, while the other end sequentially penetrates through the butting seat 10 and the shifting clamp 11 and is then detachably fixedly connected to a steel wire 13 extending from a pipeline member 12.

In the present embodiment, the pipeline member uses an existing pipeline member for a surgical robot, and a specific structure thereof will not be elaborated herein.

Preferably, a blind hole is provided in the end portion of the quick-connect shaft. A connecting pin 14 is inserted into the blind hole. Locking pin holes are provided in both the connecting pin and the shaft surface of the quick-connect shaft. A locking pin 15 is inserted into the quick-connect shaft and the connecting pin through the locking pin holes to lock and fix the connecting pin and the quick-connect shaft. The quick-connect shaft can drive the connecting pin to synchronously rotate or rectilinearly move.

The connecting pin is fixedly connected to an end portion of the steel wire. Preferably, the steel wire is fixedly connected to the connecting pin by crimping. It can be understood that those skilled in the art can select other means to fix the steel wire and the connecting pin.

Two limiting slots are provided in a position of the quick-connect shaft corresponding to the shifting clamp. A bottom slot surface of the limiting slot is a rectangular plane. The two limiting slots are located at two ends of the same diameter line of a sectional circle of the quick-connect shaft, and are provided symmetrically about the center of the circle. A portion of the quick-connect shaft between the two limiting slots forms a limiting portion 16.

The shifting clamp is arranged between the butting seat and the pipeline member and in sliding connection with the butting seat and the pipeline member, and can move in a direction perpendicular to the axes of the transmission shaft and the quick-connect shaft.

The shifting clamp is provided with a through hole. The through hole includes a first hole portion 17 and a second hole portion 18. A shape and size of the first hole portion are matched with a shape of the limiting portion. A length of the limiting portion in the axial direction of the quick-connect shaft is equal to a width of the shifting clamp. When a clamping portion is located in the first hole portion, an outer lateral surface of the limiting portion contacts with a hole surface of the first hole portion, and a lateral slot surface of the limiting slot contacts with the shifting clamp. Therefore, the rotation of the quick-connect shaft about its own axis and the rectilinear movement in its own axial direction are limited by the first hole portion, and the quick-connect shaft is further located accurately and stably.

A size of the second hole portion is larger than a section size of the quick-connect shaft. When the quick-connect shaft enters the second hole portion, a hole surface of the second hole portion does not contact with the outer lateral surface of the limiting portion, and the lateral slot surface of the limiting slot does not contact with the shifting clamp any more. At this time, the shifting clamp cannot limit the rotation of the quick-connect shaft about its own axis and the rectilinear movement in its own axial direction.

In the present embodiment, the pipeline member and the butting seat are clamped and fixed at an edge of the pipeline member. Preferably, the butting seat is provided with a butting seat clamping plate. A pipeline member clamping slot matched with the butting seat clamping plate is provided in the edge of the pipeline member. The butting seat clamping plate is inserted into the pipeline member clamping slot to implement the clamping fixation of the pipeline member and the butting seat.

It can be understood that the butting seat and the pipeline member may also be connected by bolts and other detachable fixing means. Those skilled in the art may select as practically required.

Embodiment 2

The present embodiment discloses a surgical robot, which is provided with the steel wire and transmission shaft connecting structure as described in Embodiment 1. The transmission shaft is connected to a driving mechanism. The driving mechanism can drive the transmission shaft to rotate about its own axis and rectilinearly move in its own axial direction. The driving mechanism uses an existing driving mechanism for a surgical robot, and a specific structure thereof will not be elaborated herein.

Embodiment 3

Figure 6:
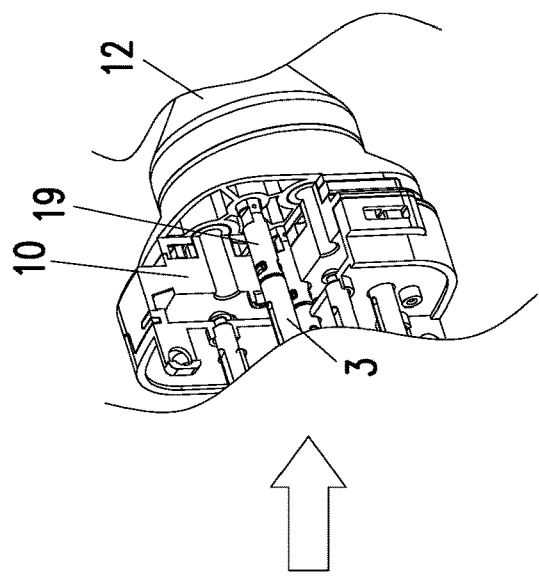
FIG. 6 is a first connecting flowchart according to Embodiment 2 of the present invention.
Figure 6:
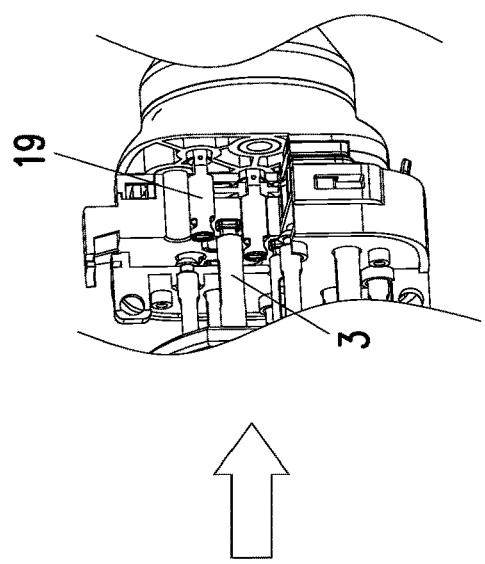
Figure 6:
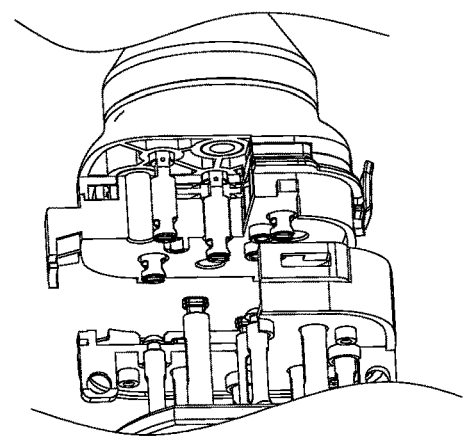
Figure 7:
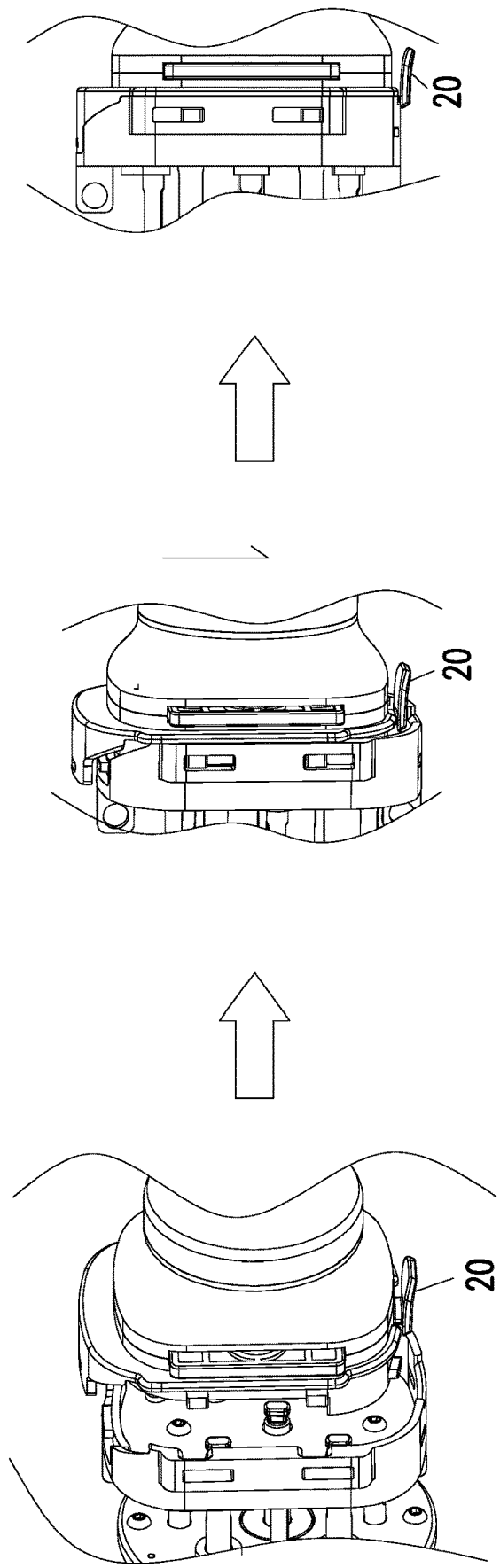
FIG. 7 is a second connecting flowchart according to Embodiment 2 of the present invention.
Figure 8:
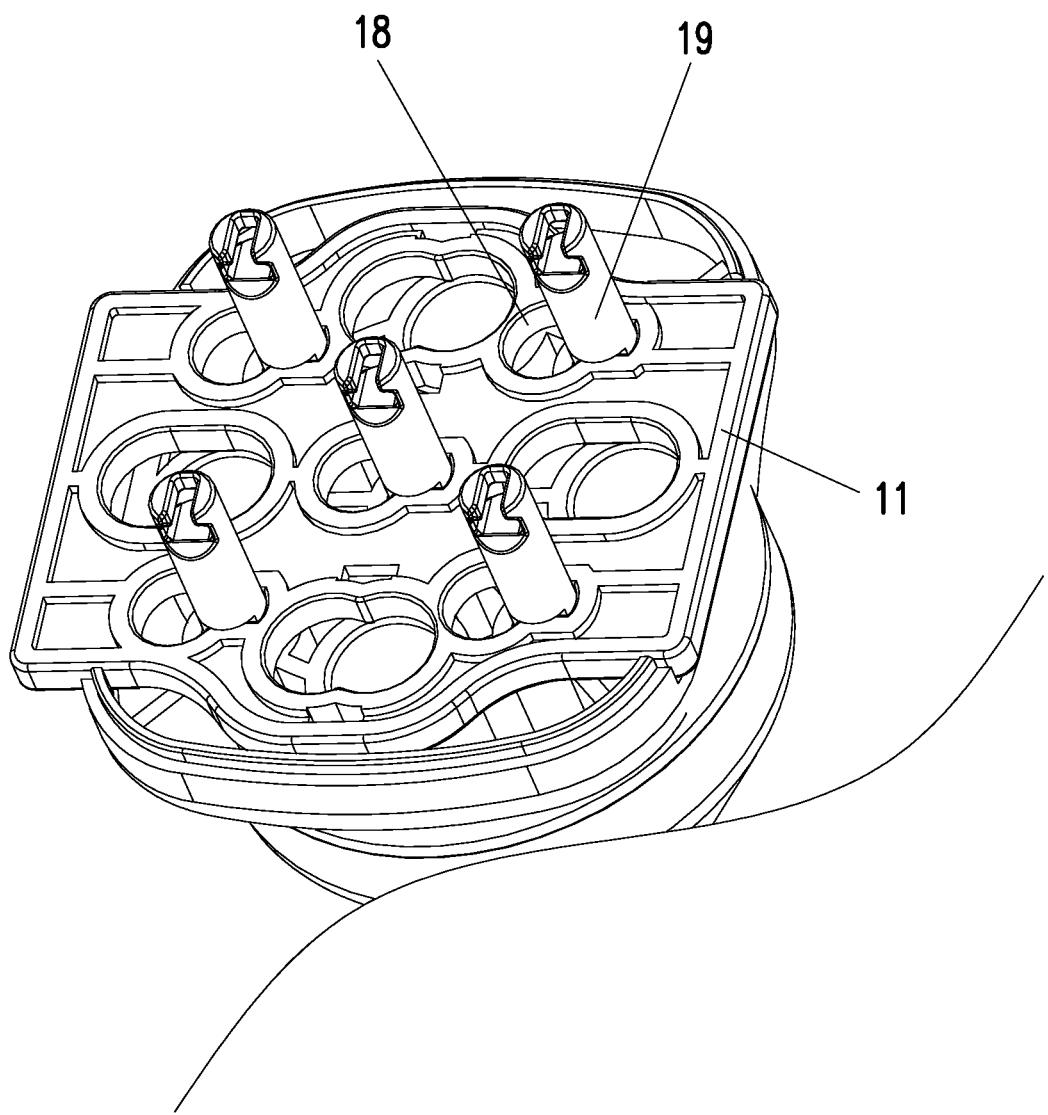
FIG. 8 is a schematic state diagram of the quick-connect shafts penetrating through a first hole portion according to Embodiment 2 of the present invention.
Figure 9:
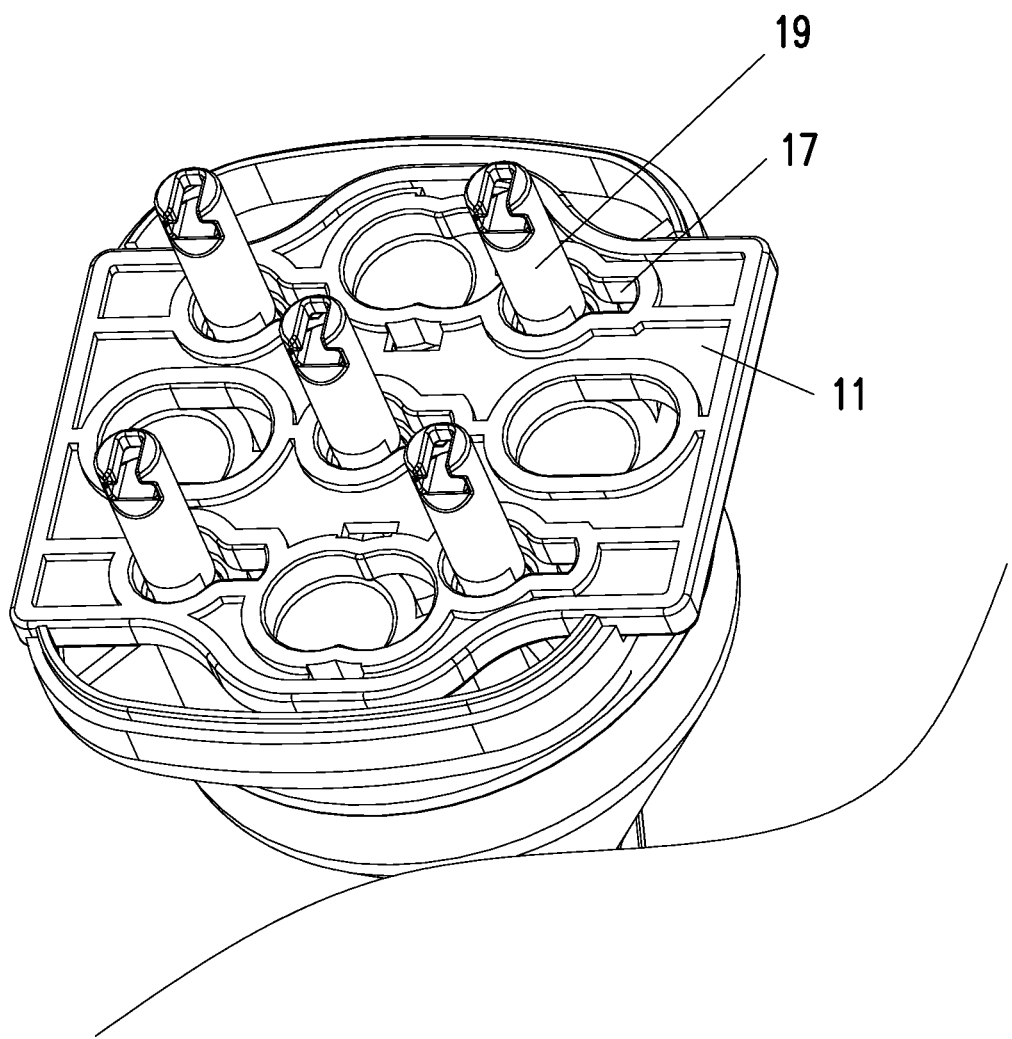
FIG. 9 is a schematic state diagram of the quick-connect shafts penetrating through a second hole portion according to Embodiment 2 of the present invention.

The present embodiment discloses a method for connecting the steel wire and transmission shaft connecting structure as described in Embodiment 1. As shown in FIGS. 6 to 9, the method includes the following steps.

After the quick-connect shaft sequentially penetrates through the butting seat and the shifting clamp in advance, the connecting pin fixed to the steel wire is inserted into the end portion of the quick-connect shaft, and is locked and fixed by the locking pin to clamp and fix the butting seat and the pipeline member. The shifting clamp is pushed such that the limiting portion of the quick-connect shaft enters the first hole portion. At this time, the quick-connect shaft is limited by the first hole portion and cannot rotate about its own axis and move in its own axial direction.

A structure consisting of the butting seat, the pipeline member, the shifting clamp, the steel wire and the quick-connect shaft is driven to move from top to bottom such that the clamping block of the transmission shaft is inserted into the groove and the second clamping block portion extends into the space between the inner lateral surface of the arc plate and the bottom groove surface of the groove, to complete the clamping fixation of the transmission shaft and the quick-connect shaft. Meanwhile, the bump of the base is inserted into the fixing hole of the butting seat to implement the fixation of the base and the butting seat.

The shifting clamp is pushed such that the quick-connect shaft enters the second hole portion. At this time, the second hole portion will not limit the quick-connect shaft to rotate about its own axis and move in its own axial direction.

When disassembling is needed, a clamped state of the buckle and the base is released, and it is only necessary to drive the structure consisting of the butting seat, the pipeline member, the shifting clamp, the steel wire and the quick-connect shaft to move upwards to separate the clamping block from the clamping slot structure. As such, disassembling can be completed.

With the connecting structure of the present embodiment, the simultaneous connection of the multiple transmission shafts and the steel wire is implemented, and separate connection of the steel wire and the transmission shaft is avoided. The whole process is convenient and efficient, the practicability is higher, the operation is more labor-saving, and the requirements on the quick connection and disassembling of driven members of multiple groups of transmission mechanisms in some situations are met.

The specific implementations of the present invention are described above with reference to the accompanying drawings, but are not intended to limit the protection scope of the present invention. A person skilled in the art should understand that various modifications or deformations may be made without creative efforts based on the technical solutions of the present invention, and such modifications or deformations shall fall within the protection scope of the present invention.

What is claimed is:

1. A steel wire and transmission shaft connecting structure, comprising a base, wherein a plurality of transmission shafts penetrate through the base; a clamping block is arranged at one end of each of the transmission shafts; each of the transmission shafts is detachably clamped and fixed to a quick-connect shaft through the clamping block and a groove which is T-shaped and provided in one end of the quick-connect shaft; an other end of the quick-connect shaft penetrates through a butting seat and is then detachably fixed to a steel wire extending from a pipeline member; a shifting clamp is arranged between the butting seat and the pipeline member; the shifting clamp is provided with a through hole configured for the quick-connect shaft to penetrate through; the through hole is composed of a first hole portion and a second hole portion; the quick-connect shaft moves between the first hole portion and the second hole portion, which can switch locked and unlocked states of the quick-connect shaft and the shifting clamp; the base is provided with a bump; the butting seat is provided with a fixed plate; a fixing hole is provided in the fixed plate; a buckle is further arranged on the butting seat; the bump can be inserted into the fixing hole at a same time when the clamping block is inserted into the groove; and the buckle is clamped and fixed to the base,
wherein a limiting slot is provided in a shaft surface of the quick-connect shaft to form a limiting portion that is inserted into the through hole; the first hole portion is configured such that a hole surface thereof fits an outer lateral surface of the limiting portion; a slot surface of the limiting slot contacts with the shifting clamp such that the first hole portion limits a movement of the quick-connect shaft; and the second hole portion is configured to have a size larger than a cross-section size of the quick-connect shaft such that the movement of the quick-connect shaft is not limited by the second hole portion.

2. The steel wire and transmission shaft connecting structure according to claim 1, wherein the clamping block is of a T-shaped structure, comprising a first clamping block portion and a second clamping block portion which are perpendicular to each other; and the first clamping block portion is fixedly connected to the corresponding transmission shaft.

3. The steel wire and transmission shaft connecting structure according to claim 2, wherein a connecting portion fixed to the quick-connect shaft is arranged at a side portion of one side of an opening of the groove; the groove and the connecting portion form a clamping slot structure together such that the clamping block can be inserted into the groove from an opposite side of the connecting portion; and the second clamping block portion extends from a space between the connecting portion and a bottom groove surface of the groove to implement a clamping fixation of the clamping block and the quick-connect shaft.

4. The steel wire and transmission shaft connecting structure according to claim 1, wherein the butting seat is fixedly connected to the pipeline member.

5. The steel wire and transmission shaft connecting structure according to claim 1, wherein the end of the quick-connect shaft is detachably connected to the corresponding transmission shaft, while a connecting pin is inserted into the other end; the connecting pin is locked and fixed to the quick-connect shaft through a locking pin; and the connecting pin is fixedly connected to the steel wire.

6. The steel wire and transmission shaft connecting structure according to claim 5, wherein the steel wire and the connecting pin are fixed by crimping.

7. A surgical robot, provided with the steel wire and transmission shaft connecting structure according to claim 1.

8. A method for connecting the steel wire and transmission shaft connecting structure according to claim 1, comprising:
pushing the shifting clamp such that the quick-connect shaft penetrates through the first hole portion, to limit the movement of the quick-connect shaft by the shifting clamp;
moving an assembly comprising the butting seat, the pipeline member, the shifting clamp, the steel wire, and the quick-connect shaft from top to bottom, such that the clamping block at the end of the transmission shaft is embedded into a clamping slot structure, to complete a clamping fixation of the transmission shaft and the quick-connect shaft, and concurrently the bump of the base is inserted into the fixing hole of the butting seat, to secure the base to the butting seat; and pushing the shifting clamp such that the quick-connect shaft penetrates through the second hole portion, to remove a limitation of the shifting clamp to the movement of the quick-connect shaft.

\* \* \* \* \*